United States Patent [19]

Ishida et al.

[11] Patent Number: 5,755,833
[45] Date of Patent: May 26, 1998

[54] FUEL ADDITIVE

[75] Inventors: Noboru Ishida; Masaki Nagao; Takashi Kaneko, all of Yokohama, Japan

[73] Assignee: Nippon Oil Co., Ltd., Tokyo, Japan

[21] Appl. No.: 589,664

[22] Filed: Jan. 22, 1996

[30] Foreign Application Priority Data

Jan. 23, 1995 [JP] Japan ................ 7-027324

[51] Int. Cl.$^6$ .................................................. C10L 1/22
[52] U.S. Cl. ........................ 44/333; 44/334; 44/335; 44/387
[58] Field of Search ........................ 44/387, 332, 333, 44/334, 335; 252/51.5 A, 51.5 R; 508/248, 249, 259, 513; 560/158, 159, 166

[56] References Cited

U.S. PATENT DOCUMENTS

| | | |
|---|---|---|
| 2,522,155 | 9/1950 | Ballard et al. . |
| 3,359,303 | 12/1967 | Coker et al. . |
| 4,160,648 | 7/1979 | Lewis et al. . |
| 4,191,537 | 3/1980 | Lewis et al. ............... 44/387 |
| 4,197,409 | 4/1980 | Lilburn ....................... 44/387 |
| 4,274,837 | 6/1981 | Lilburn . |
| 4,521,610 | 6/1985 | Plavac ........................ 44/387 |
| 4,933,485 | 6/1990 | Buckley, III ............... 44/387 |
| 4,975,096 | 12/1990 | Buckley, III ............... 44/433 |
| 5,192,335 | 3/1993 | Cherpeck ................... 44/387 |
| 5,268,243 | 12/1993 | Noda et al. ............... 252/62.2 |
| 5,269,955 | 12/1993 | Kawaguchi et al. ....... 252/68 |
| 5,306,314 | 4/1994 | Cherpeck ................... 44/387 |
| 5,312,460 | 5/1994 | Buckley, III ............... 44/387 |
| 5,312,965 | 5/1994 | Buckley ................. 252/51.5 R |
| 5,322,529 | 6/1994 | Buckley, III ............... 44/387 |
| 5,364,546 | 11/1994 | Buckley, III ............ 252/51.5 A |
| 5,413,614 | 5/1995 | Cherpeck ................... 44/387 |
| 5,413,615 | 5/1995 | Cherpeck ................... 44/387 |
| 5,484,463 | 1/1996 | Cherpeck ................... 44/387 |

FOREIGN PATENT DOCUMENTS

| | | |
|---|---|---|
| 0 298 636-A1 | 1/1989 | European Pat. Off. . |
| 0 397 037-A2 | 11/1990 | European Pat. Off. . |
| 0 559 317-A1 | 9/1993 | European Pat. Off. . |
| A-647266 | 12/1950 | United Kingdom . |

*Primary Examiner*—Margaret Medley
*Attorney, Agent, or Firm*—Panitch Schwarze Jacobs & Nadel, P.C.

[57] ABSTRACT

A fuel additive comprising a urethane compound. A gasoline composition comprising gasoline blended with a urethane compound to suppress sludge or deposits in fuel intake systems or combustion chambers, such as an automobile engine.

4 Claims, No Drawings

FUEL ADDITIVE

BACKGROUND OF THE INVENTION

1. Field of the Invention

This invention relates to oil additives and fuel compositions incorporating such additives.

2. Prior Art

Sludge or other objectionable deposits if formed in internal combustion engine fuel systems or combustion chambers of automobiles are responsible for engine trouble or abnormal rise in carbon monoxide and unburnt hydrocarbon concentrations in the exhaust gases. It has thus far been proposed to use certain fuel additives, typically a gasoline detergent such as a polyether amine-based or polyamine-based detergent for removing or otherwise preventing deposits in the carburetor, electronic fuel injections, intake valves and other internal operative parts of the automobile. Additives to this end are disclosed in U.S. Pat. Nos. 4,247,301 and 4,160,648 wherein a polyether-based gasoline detergent dispersant is recited as effective in removing or controlling deposits particularly on the fuel intake system.

Intensive research efforts have been made in the automobile industry to eliminate or alleviate the adverse effect of exhaust gases upon the human body and the environment is parallel with the effort for fuel consumption reduction. With this background in view, there has been a growing demand for more effective and advantageous gasoline additives such that may serve to maintain cleanliness of fuel intake systems and combustion chambers particularly when the engine is cool.

It has now been found that urethane compounds of a selected structure can exhibit surprisingly high deterging performance when blended with gasoline fuels.

SUMMARY OF THE INVENTION

The present invention seeks to provide a novel fuel additive which is in itself highly resistant to sludge or deposit formation and which has excellent detergent capabilities.

The invention further seeks to provide a fuel composition which incorporates such a novel additive.

According to the invention, there is provided a fuel additive which comprises a urethane compound of the formula

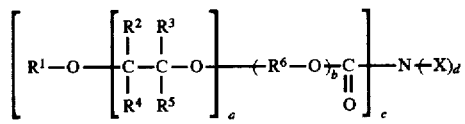

wherein $R^1$ is hydrogen or a $C_1$–$C_{30}$ hydrocarbon group, $R^2$, $R^3$, $R^4$ and $R^5$ each are hydrogen or a $C_1$–$C_{10}$ hydrocarbon group and at least one of them is a group of formula (II) below, $R^6$ is a $C_2$–$C_6$ alkylene group, a is an integer of 1–100, b is an integer of 0–100, the sum of a and b being equal to 1–200, c is an integer of 1–3, d is an integer of 0–2, the sum of c and d being equal to 3, and X is selected from the group consisting of hydrogen, a $C_1$–$C_{30}$ hydrocarbon group, a group of formula (III) below and a group of formula (IV) below;

said formula (II) being represented by

wherein $R^7$ and $R^8$ each are hydrogen, a $C_1$–$C_{10}$ hydrocarbon group or a $C_2$–$C_{10}$ alkoxyalkyl group, $R^9$ is a $C_2$–$C_6$ alkylene group or a $C_4$–$C_{10}$ alkylene group having an alkoxyalkyl substituent, $R^{10}$ is hydrogen or a $C_1$–$C_{30}$ hydrocarbon group, and e is an integer of 0–50;

said formula (III) being represented by

wherein $R^{11}$ is a $C_2$–$C_6$ alkylene group, $R^{12}$ is hydrogen or a $C_1$–$C_4$ alkyl group, $R^{13}$ is hydrogen or a $C_1$–$C_{30}$ hydrocarbon group, and f is an integer of 1–5;

and said formula (IV) being represented by

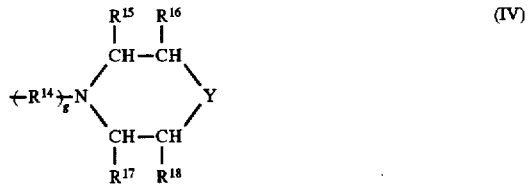

wherein $R^{14}$ is a $C_2$–$C_6$ alkylene group, $R^{15}$, $R^{16}$, $R^{17}$ and $R^{18}$ each are hydrogen or a $C_1$–$C_{10}$ hydrocarbon group, Y is a methylene group, a $C_1$–$C_{10}$ hydrocarbon-substituted methylene group, an imino group, a $C_1$–$C_{10}$ hydrocarbon-substituted imino group or oxygen, g is 1 if d is equal to 1 and 0 or 1 if d is equal to 2, and if g is equal to 0, N here corresponds to N in formula (I).

The above and other features and advantages of the invention will be better understood from the following detailed description.

DETAILED DESCRIPTION OF THE INVENTION

The term oil as used herein generally designates liquid hydrocarbons boiling in the range of between 30° C. and 700° C., preferably 40° C. and 600° C. primarily intended for combustion and derivable from petroleum, wastes, oil shale, oil sand, coal, biomass. However, the liquid hydrocarbons containing crude oil or petroleum fractions as main component should be used. The crude oil includes paraffin-based crude oil, naphthene-based crude oil, mixed crude oil, special crude oil and mixtures thereof. The petroleum fractions include products from distillation, cracking and reformation of the crude oil and its mixtures and specifically encompass gasoline fractions for automobile engines and various internal combustion engines, naphtha fractions (light, heavy and whole-range), jet fuel, aviation gasoline, kerosine for air-conditioning, cooking, motor drive and the like, gas oil fractions for diesel engines and fuels, heavy oil fractions (A, B and C) for boilers, air-conditioners, marine diesel engines and ceramics, and mixtures thereof.

The term wastes includes city and industrial wastes and spent oils that may be recycled into useful liquid hydrocarbon fuels.

The inventive urethane compound finds advantageous use as an additive to gasolines (such as automobile gasolines of JIS K 2202) for internal combustion engines in particular as it exhibits prominent deterging ability to maintain cleanliness of fuel intake systems and combustion chambers.

A fuel additive according to the invention comprises a urethane compound of the formula

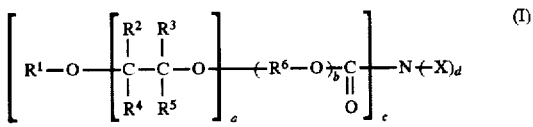 (I)

wherein $R^1$ is hydrogen or a $C_1$–$C_{30}$ hydrocarbon group, $R^2$, $R^3$, $R^4$ and $R^5$ each are hydrogen or a $C_1$–$C_{10}$ hydrocarbon group and at least one of them is a group of formula (II) below, $R^6$ is a $C_2$–$C_6$ alkylene group, a is an integer of 1–100, b is an integer of 0–100, the sum of a and b being equal to 1–200, c is an integer of 1–3, d is an integer of 0–2, the sum of c and d being equal to 3, and X is selected from the group consisting of hydrogen, a $C_1$–$C_{30}$ hydrocarbon group, a group of formula (III) below and a group of formula (IV) below;

said formula (II) being represented by

 (II)

wherein $R^7$ and $R^8$ each are hydrogen, a $C_1$–$C_{10}$ hydrocarbon group or a $C_2$–$C_{10}$ alkoxyalkyl group, $R^9$ is a $C_2$–$C_6$ alkylene group or a $C_4$–$C_{10}$ alkylene group having an alkoxyalkyl substituent, $R^{10}$ is hydrogen or a $C_1$–$C_{30}$ hydrocarbon group, and e is an integer of 0–50;

said formula (III) being represented by

 (III)

wherein $R^{11}$ is a $C_2$–$C_6$ alkylene group, $R^{12}$ is hydrogen or a $C_1$–$C_4$ alkyl group, $R^{13}$ is hydrogen or a $C_1$–$C_{30}$ hydrocarbon group, and f is an integer of 1–5;

and said formula (IV) being represented by

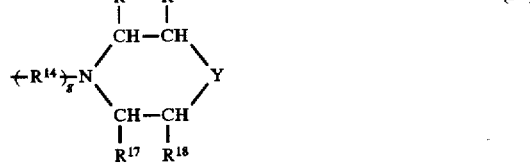 (IV)

wherein $R^{14}$ is a $C_2$–$C_6$ alkylene group, $R^{15}$, $R^{16}$, $R^{17}$ and $R^{18}$ each are hydrogen or a $C_1$–$C_{10}$ hydrocarbon group, Y is a methylene group, a $C_1$–$C_{10}$ hydrocarbon-substituted methylene group, an imino group, a $C_1$–$C_{10}$ hydrocarbon-substituted imino group or oxygen, g is 1 if d is equal to 1 and 0 or 1 if d is equal to 2, and if g is equal to 0, N here corresponds to N in formula (I).

More specifically, $R^1$ in formula (I) is preferably hydrogen, a $C_1$–$C_{24}$ straight or branched alkyl group, a $C_2$–$C_{24}$ straight or branched alkenyl group, a $C_5$–$C_{13}$ cycloalkyl or alkylcycloalkyl group, a $C_6$–$C_{18}$ aryl or alkylaryl group, or a $C_7$–$C_{19}$ arylalkyl group.

Preferred examples of alkyl group $R^1$ include methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl, straight or branched decyl, straight or branched undecyl, straight or branched dodecyl, straight or branched tridecyl, straight or branched tetradecyl, straight or branched pentadecyl, straight or branched hexadecyl, straight or branched heptadecyl, straight or branched octadecyl, straight or branched nonadecyl, straight or branched icosyl, straight or branched heneicosyl, straight or branched docosyl, straight or branched tricosyl and straight or branched tetracosyl.

Preferred examples of alkenyl group $R^1$ include vinyl, propenyl, isopropenyl, straight or branched butenyl, butadienyl, straight or branched pentenyl, straight or branched hexenyl, straight or branched heptenyl, straight or branched octenyl, straight or branched nonenyl, straight or branched decenyl, straight or branched undecenyl, straight or branched dodecenyl, straight or branched tridecenyl, straight or branched tetradecenyl, straight or branched pentadecenyl, straight or branched hexadecenyl, straight or branched heptadecenyl, straight or branched octadecenyl such as denyl, straight or branched nonadecenyl, straight or branched icosenyl, straight or branched heneicosenyl, straight or branched docosenyl, straight or branched tricosenyl and straight or branched tetracosenyl.

Preferred examples of cycloalkyl group $R^1$ include cyclopentyl, cyclohexyl and cycloheptyl, and alkylcycloalkyl group $R^1$ include methyl cyclopentyl, dimethylcyclopentyl (inclusive of all isomers), ethylcyclopentyl (inclusive of all isomers), straight or branched propylcyclopentyl (inclusive of all isomers), ethylmethylcyclopentyl (inclusive of all isomers), trimethylcyclopentyl (inclusive of all isomers), diethylcyclopentyl) inclusive of all isomers), ethyldimethylcyclopentyl) inclusive of all isomers), straight or branched propylmethylcyclopentyl (inclusive of all isomers), straight or branched propylethylcyclopentyl (inclusive of all isomers), di-straight or branched propylcyclopentyl (inclusive of all isomers), straight or branched propylethylmethylcyclopentyl (inclusive of all isomers), metylcyclohexyl (inclusive of all isomers), dimethylcyclohexyl (inclusive of all isomers), ethylcyclohexyl (inclusive of all isomers, straight or branched propylcyclohexyl (inclusive of all isomers), ethylmethylcyclohexyl (inclusive of all isomers), trimethylcyclohexyl (inclusive of all isomers), diethylcyclohexyl (inclusive of all isomers), ethyldimethylcyclohexyl (inclusive of all isomers), straight or branched propylmethylcyclohexyl (inclusive of all isomers), straight or branched propylethylcyclohexyl (inclusive of all isomers), di-straight or branched propylcyclohexyl (inclusive of all isomers), straight or branched propylethylmethylcyclohexyl (inclusive of all isomers), metylcycloheptyl (inclusive of all isomers), dimethycycloheptyl (inclusive of all isomers), ethylcycloheptyl (inclusive of all iosmers), straight or branched propylcycloheptyl (inclusive of all isomers), ethylmethylcycloheptyl (inclusive of all isomers), trimethylcycloheptyl (inclusive of all isomers), diethylcycloheptyl (inclusive of all isomers), ethyldimethylcycloheptyl (inclusive of all isomers), straight or branched propylmethylcycloheptyl (inclusive of all isomers), straight or branched propylethylcycloheptyl (inclusive of all isomers), di-straight or branched propylcycloheptyl (inclusive of all iosmers), and straight or branched propylethylmethylcycloheptyl (inclusive of all isomers).

Preferred examples of aryl group $R^1$ include phenyl and naphthyl, and alkylaryl group $R^1$ include tolyl (inclusive of all isomers), xylyl (inclusive of all isomers), ethylphenyl (inclusive of all isomers), straight or branched propylphenyl (inclusive of all isomers), ethylmethylphenyl (inclusive of all isomers), trimethylphenyl (inclusive of all isomers), straight or branched butylphenyl (inclusive of all isomers), straight or branched propylmethylphenyl (inclusive of all isomers), diethylphenyl (inclusive of all isomers), ethyldimethylphenyl (inclusive of all isomers), tetramethylphenyl (inclusive of all isomers), straight or branched pentylphenyl (inclusive of all isomers), straight or branched hexylphenyl (inclusive of all isomers), straight or branched heptylphenyl (inclusive of all isomers), straight or branched octylphenyl (inclusive of all isomers), straight or branched nonylphenyl (inclusive of all isomers), straight or branched decylphenyl (inclusive of all isomers), straight or branched undecylphenyl (inclusive of all isomers) and straight or branched dodcylphenyl (inclusive of all isomers), and further arylalkyl group $R^1$ include benzyl, methylbenzyl (inclusive of all isomers), dimethylbenzyl (inclusive of all isomers), phenethyl, methylphenethyl (inclusive of all isomers) and dimethylphenethyl (inclusive of all isomers).

Particularly preferred $R^1$ examples are a $C_1$–$C_{12}$ straight or branched alkyl group and a $C_6$–$C_{12}$ aryl or alkylaryl group, and more preferably a $C_1$–$C_6$ straight or branched alkyl group or phenyl group and a $C_7$–$C_9$ straight or branched alkylaryl group.

$R^2$, $R^3$, $R^4$ and $R^5$ each in formula (I) designate $C_1$–$C_{10}$ hydrocarbon group encompassing a $C_1$–$C_{10}$ straight or branched alkyl group, a $C_2$–$C_{10}$ straight or branched alkenyl group, a $C_5$–$C_{10}$ cycloalkyl or alkylcycloalkyl group, a $C_6$–$C_{10}$ aryl or alkylaryl group and a $C_7$–$C_{10}$ arylalkyl group. Preferred examples of alkyl group include methyl, ethyl, n-propyl, isopropyl, n-butyl, isobutyl, sec-butyl, tert-butyl, straight or branched pentyl, straight or branched hexyl, straight or branched heptyl, straight or branched octyl, straight or branched nonyl and straight or branched decyl, and alkonyl group include vinyl, propenyl, isopropenyl, straight or branched butenyl, butadienyl, straight or branched pentenyl, straight or branched hexyl, straight or branched heptenyl, straight or branched octenyl, straight or branched nonenyl and straight or branched decenyl.

Preferred examples of cycloalkyl group include cyclopentyl, cyclohexyl and cycloheptyl, and alkylcycloalkyl group include methylcyclopentyl (inclusive of all isomers), dimethylcyclopentyl (inclusive of all isomers), ethylcyclopentyl (inclusive of all isomers), straight or branched propylcyclopentyl (inclusive of all isomers), ethylmethylcyclopentyl (inclusive of all isomers), trimethylcyclopentyl (inclusive of all isomers), diethylcyclopentyl (inclusive of all isomers), ethyldimethylcyclopentyl (inclusive of all isomers), straight or branched propylmethylcyclopentyl (inclusive of all isomers), straight or branched propylethylcyclopentyl (inclusive of all isomers), methylcyclohexyl (inclusive of all isomers), dimethylcyclohexyl (inclusive of all isomers), ethylcyclohexyl (inclusive of all isomers), straight or branched propylcyclohexyl (inclusive of all isomers), ethylmethylcyclohexyl (inclusive of all isomers), trimethylcyclohexyl (inclusive of all isomers), diethylcyclohexyl (inclusive of all isomers), ethyldimethylcyclohexyl (inclusive of all isomers), straight or branched propylmethylcyclohexyl (inclusive of all isomers), methylcycloheptyl (inclusive of all isomers), dimethylcycloheptyl (inclusive of all isomers), ethylcycloheptyl (inclusive of all isomers), straight or branched propylcycloheptyl (inclusive of all isomers), ethylmethylcycloheptyl (inclusive of all isomers) and trimethylcycloheptyl (inclusive of all isomers).

Preferred examples of aryl group include phenyl and naphthyl, and alkylaryl group include tolyl (inclusive of all isomers), xylyl (inclusive of all isomers), ethylphenyl (inclusive of all isomers), straight or branched propylphenyl (inclusive of all isomers), ethylmethylphenyl (inclusive of all isomers), trimethylphenyl (inclusive of all isomers), straight or branched butylphenyl (inclusive of all isomers), straight or branched propylmethylphenyl (inclusive of all isomers), diethylphenyl (inclusive of all isomers), ethyldimethylphenyl (inclusive of all isomers) and tetramethylphenyl (inclusive of all isomers), and further arylalkyl group include benzyl, methylbenzyl (inclusive of all isomers), dimethylbenzyl (inclusive of all isomers), phenethyl, methyl phenethyl (inclusive of all isomers) and dimethylphenethyl (inclusive of all isomers).

Particularly preferred among the above $C_1$–$C_{10}$ hydrocarbon groups is a $C_1$–$C_6$, preferably $C_1$–$C_3$, straight or branched alkyl group.

At least one of $R^2$–$R^5$ is a group of the formula (II) above wherein $R^7$ and $R^8$ each are hydrogen, a $C_1$–$C_{10}$ hydrocarbon group or a $C_2$–$C_{10}$ alcoxyalkyl group. The term $C_1$–$C_{10}$ hydrocarbon group here encompasses all of the groups already identified with regard to $R^2$–$R^5$.

Alcoxyalkyl groups of the formula (II) exemplarily include methoxymethyl, ethoxymethyl, n-propoxymethyl, isopropoxymethyl, n-butoxymethyl, isobutoxymethyl, sec-butoxymethyl, tert-butoxymethyl, pentoxymethyl (inclusive of all isomers), hexoxymethyl (inclusive of all isomers), heptoxymethyl (inclusive of all isomers), octoxymethyl (inclusive of all isomers), nonyloxymethyl (inclusive of all isomers), methoxyethyl (inclusive of all isomers), ethoxyethyl (inclusive of all isomers), propoxyethyl (inclusive of all isomers), butoxyethyl (inclusive of all isomers), pentoxyethyl (inclusive of all isomers), hexoxyethyl (inclusive of all isomers), heptoxyethyl (inclusive of all isomers), octoxyethyl (inclusive of all isomers), methoxypropyl (inclusive of all isomers), ethoxypropyl (inclusive of all isomers), propoxypropyl (inclusive of all isomers), butoxypropyl (inclusive of all isomers), pentoxypropyl (inclusive of all isomers), hexoxypropyl (inclusive of all isomers), heptoxypropyl (inclusive of all isomers), methoxybutyl (inclusive of all isomers), ethoxybutyl (inclusive of all isomers), propoxybutyl (inclusive of all isomers), botoxybutyl (inclusive of all isomers), pentoxybutyl (inclusive of all isomers), hexoxybutyl (inclusive of all isomers), methoxypentyl (inclusive of all isomers), ethoxypentyl (inclusive of all isomers), propoxypentyl (inclusive of all isomers), butoxypentyl (inclusive of all isomers), pentoxypentyl (inclusive of all isomers), methoxyhexyl (inclusive of all isomers), ethoxyhexyl (inclusive of all isomers), propoxyhexyl (inclusive of all isomers), butoxyhexyl (inclusive of all isomers), methoxyheptyl (inclusive of all isomers), ethoxyheptyl (inclusive of all isomers), propoxyheptyl (inclusive of all isomers), methoxyoctyl (inclusive of all isomers), ethoxyoctyl (inclusive of all isomers) and methoxynonyl (inclusive of all isomers).

$R^7$ and $R^8$ in formula (II) each are preferably hydrogen, a $C_1$–$C_6$ alkyl group or a $C_2$–$C_6$ alcoxyalkyl group, of which hydrogen and $C_1$–$C_3$ alkyl groups are more preferred.

$R^9$ in formula (II) designates a $C_2$–$C_6$ alkylene group or a $C_4$–$C_{10}$ alkylene group having an alkoxyalkyl substituent. The $C_2$–$C_6$ alkylene group exemplarily includes ethylene, propylene (1-methylethylene, 2-methylethylene), trimethylene, butylene (1-ethyethylene, 2-ethylethylene), 1,2-dimethylethylene, 2,2-dimethylethylene, 1-methyltrimethylene, 2-methyltrimethylene, 3-methyltrimethylene, tetramethylene, pentylene (1-butylethylene, 2-butylethylene), 1-ethyl-1-metylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,1-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, hexylene (1-butylethylene, 2-butylethylene), 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-metyltrimethylene, 2-ethly-1-methyltrimethylene, 2-ethyl-2-methyltrimethylene, 2-ethyl-3-methyltrimethylene, 3-ethyl-1-methyltrimethylene, 3-ethyl-2-metyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene and hexamethylene.

The $C_4$–$C_{10}$ alkylene group having an alkoxyalkyl substituent referred to as $R^9$ in formula (II) exemplarily includes a $C_2$–$C_8$ alkoxyalkyl substituted ethylene such as 1-(methoxymethyl)ethylene, 2-(methoxymethyl)ethylene, 1-(methoxyethyl)ethylene, 2-(methoxyethyl)ethylene, 1-(ethoxymethyl)ethylene, 2-(ethoxymethyl)ethylene, 1-methoxymethyl-2-methylethylene, 1,1-bis(methoxymetyl)ethylene, 2,2-bis(methoxymethyl)ethylene, 1,2-bis(methoxymethyl)ethylene, 1,1-bis(methoxyethyl)ethylene, 2,2-bis(methoxyethyl)ethylene, 1,2-bis(methoxyethyl)ethylene, 1,1-bis(ethoxymethyl)ethylene, 2,2-bis(ethoxymethyl)ethylene, 1,2-bis(ethoxymethyl)ethylene, 1-methyl-2-methoxymethylethylene, 1-methoxymethyl-2-methylethylene, 1-ethyl-2-methoxymethylethylene, 1-methoxymethyl-2-ethylethylene, 1-methyl-2-ethoxymethylethylene, 1-ethoxymethyl-2-methylethylene, 1-ethyl-2-ethoxymethylethylene, 1-ethoxymethyl-2-ethylethylene, 1-methyl-2-methoxyethylethylene and 1-methoxyethyl-2-ethylethylene.

$R^9$ in formula (II) is preferably a $C_2$–$C_4$ alkylene group or an ethylene group substituted with a $C_2$–$C_6$ alkoxyalkyl.

$R^{10}$ in formula (II) is hydrogen or a $C_1$–$C_{30}$ hydrocarbon group, alternatively either of the groups identified with regard to $R^1$ in formula (I). Particularly preferred is a $C_1$–$C_{24}$, more preferably $C_1$–$C_{12}$ alkyl group.

The designation e in formula (II) is an integer of between 0 and 50, preferably between 0 and 30, more preferably between 0 and 20.

The group of the formula (II) may be conveniently hereinafter called a "preferred substituent" where $R^7$ and $R^8$ each are hydrogen, a $C_1$–$C_6$ alkyl group or a $C_2$–$C_6$ alkoxyalkyl group, $R^9$ is a $C_2$–$C_6$ alkylene group or a $C_2$–$C_8$ alkoxyalkyl substituted with an ethylene, $R^{10}$ is a $C_1$–$C_{24}$ alkyl group and e is an integer of between 0 and 30, and a "more preferred substituent" where $R^7$ and $R^8$ each are hydrogen or a $C_1$–$C_3$ alkyl group, $R^9$ is a $C_2$–$C_4$ alkylene group, $R^{10}$ is a $C_1$–$C_{12}$ alkyl group and e is an integer of between 0 and 20.

Importantly, at least one of $R^2$, $R^3$, $R^4$ and $R^5$ in formula (I) is the group represented by formula (II). Preferably, one or two of $R^2$–$R^5$ groups are selected from formula (II), while the remaining three or two groups each are hydrogen or a $C_1$–$C_6$ alkyl group. More preferably, one of $R^2$–$C^5$ groups is the above-mentioned "preferred substituent" or "more preferred substituent", while the remaining three each are hydrogen or a $C_1$–$C_3$ alkyl group.

$R^6$ in formula (I) is a $C_2$–$C_6$ alkylene group encompassing ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene, tetramethylene, pentylene (1-butylethylene, 2-butylethylene), 1-ethyl-1-metylethylene, 1-ethyl-2-methylethylene, 1,1,2-trimethylethylene, 1,2,2-trimethylethylene, 1-ethyltrimethylene, 2-ethyltrimethylene, 3-ethyltrimethylene, 1,2-dimethyltrimethylene, 1,2-dimethyltrimethylene, 1,3-dimethyltrimethylene, 2,3-dimethyltrimethylene, 3,3-dimethyltrimethylene, 1-methyltetramethylene, 2-methyltetramethylene, 3-methyltetramethylene, 4-methyltetramethylene, pentamethylene, hexylene (1-butylethylene, 2-butylethylene), 1-methyl-1-propylethylene, 1-methyl-2-propylethylene, 2-methyl-2-propylethylene, 1,1-diethylethylene, 1,2-diethylethylene, 2,2-diethylethylene, 1-ethyl-1,2-dimethylethylene, 1-ethyl-2,2-dimethylethylene, 2-ethyl-1,1-dimethylethylene, 2-ethyl-1,2-dimethylethylene, 1,1,2,2-tetramethylethylene, 1-propyltrimethylene, 2-propyltrimethylene, 3-propyltrimethylene, 1-ethyl-1-methyltrimethylene, 1-ethyl-2-methyltrimethylene, 1-ethyl-3-methyltrimethylene, 2-ethyl-1-methyltrimethylene, 2-ethyl-2-methyltrimethylene, 2-ethyl-3-methyltrimethylene, 3-ethyl-1-methyltrimethylene, 3-ethyl-2-methyltrimethylene, 3-ethyl-3-methyltrimethylene, 1,1,2-trimethyltrimethylene, 1,1,3-trimethyltrimethylene, 1,2,2-trimethyltrimethylene, 1,2,3-trimethyltrimethylene, 1,3,3-trimethyltrimethylene, 2,2,3-trimethyltrimethylene, 2,3,3-trimethyltrimethylene, 1-ethyltetramethylene, 2-ethyltetramethylene, 3-ethyltetramethylene, 4-ethyltetramethylene, 1,1-dimethyltetramethylene, 1,2-dimethyltetramethylene, 1,3-dimethyltetramethylene, 1,4-dimethyltetramethylene, 2,2-dimethyltetramethylene, 2,3-dimethyltetramethylene, 2,4-dimethyltetramethylene, 3,3-dimethyltetramethylene, 3,4-dimethyltetramethylene, 4,4-dimethyltetramethylene, 1-methylpentamethylene, 2-methylpentamethylene, 3-methylpentamethylene, 4-methylpentamethylene, 5-methylpentamethylene and hexamethylene.

Particularly preferred is a $C_2$–$C_4$ alkylene group such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene.

In formula (I) representing the inventive urethane compound, a is an integer of between 1 and 100, preferably between 5 and 50 and b is an integer of between 0 and 100, preferably between 0 and 50, the sum of a and b being equal to between 1 and 200, preferably between 5 and 100.

The inventive urethane compound further has a group of the formula

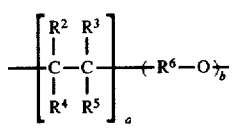

The above group includes 1–100, preferably 5–50, more preferably 5–30 of a constituent unit of the formula

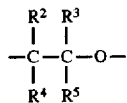

and 0–100, preferably 0–50, more preferably 0–30 of a constituent unit of the formula

The sum of constituent units (VI) and (VII) is between 1 and 200, preferably 5 and 100.

The group represented by formula (V) is a group derivable from the following polymers:

(1) Homopolymer consisting of one of the constituent units of formula (VI). (b=0)

(2) Random-, alternating- or block-copolymer consisting of two or more of different constituent units of formula (VI). (b≠0)

(3) Random-, alternating- or block-copolymer consisting of one of the constituent units (VI) and one of the constituent units (VII). (b=0)

(4) Random-, alternating- or block-copolymer consisting of two or more of different constituent units (VI) and one of the constituent units (VII). (b≠0)

(5) Random-, alternating- or block-copolymer consisting of one of the constituent units (VI) and two or more of different constituent units (VII). (b≠0)

(6) Random-, alternating- or block-copolymer consisting of two or more of different constituent units (VI) and two or more of different constituent units (VII). (b≠0)

In formula (I) the constituent units (VI) and (VII) are shown bonded to $R^1$—O— group and (—C(=O)—) group, respectively. This representation is arbitrary and may be reversed or at random in order.

In formula (I), c is an integer of between 1 and 3, preferably between 1 and 2 and more preferably 1, d is an integer of between 0 and 2, preferably between 1 and 2 and more preferably 2, the sum of c and d being equal to 3.

In formula (I), X is selected from any one of the following:

(A) Hydrogen (B) $C_1$–$C_{30}$ hydrocarbon groups (C) Groups of the formula

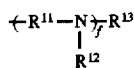

wherein $R^{11}$ is a $C_2$–$C_6$ alkylene group, $R^{12}$ is hydrogen or a $C_1$–$C_4$ alkyl group, $R^{13}$ is hydrogen or a $C_1$–$C_{30}$ hydrocarbon group, and f is an integer of 1–5.

(D) Groups of the formula

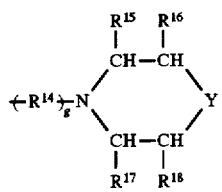

wherein $R^{14}$ is a $C_2$–$C_6$ alkylene group, $R^{15}$, $R^{16}$, $R^{17}$ and $R^{18}$ each are hydrogen or a $C_1$–$C_{10}$ hydrocarbon group, Y is a methylene group, a $C_1$–$C_{10}$ hydrocarbon-substituted methylene group, an imino group, a $C_1$–$C_{10}$ hydrocarbon-substituted imino group or oxygen, g is 1 if d is equal to 1 and 0 or 1 if d is equal to 2, and if g is equal to 0, N here corresponds to N in formula (I).

The $C_1$–$C_{30}$ hydrocarbon group (D) is as identified hereinabove and preferably a $C_1$–$C_{12}$ straight or branched alkyl group or a $C_6$–$C_{12}$ aryl or alkylaryl group, more preferably a $C_1$–$C_6$ alkyl or phenyl group, and a $C_7$–$C_9$ alkylaryl group.

The group of formula (III) above includes an alkylene group $R^{11}$ including the above-mentioned alkylene group of $R^6$. Particularly preferred is a $C_2$–$C_4$ alkylene group such as ethylene, propylene (1-methylethylene, 2-methylethylene), trimethylene, butylene (1-ethylethylene, 2-ethylethylene), 1,2-dimethylethylene, 2,2-dimethylethylene, 1-methyltrimethylene, 2-methyltrimethylene, 3-methyltrimethylene and tetramethylene, more preferably ethylene, propylene (1-methylethylene, 2-methylethylene) and trimethylene.

The group $R^{12}$ is hydrogen or a $C_1$–$C_4$ alkyl group such as methyl, ethyl, n-propyl, isopropyl, n-butyl, isobutyl, sec-butyl and tert-butyl, preferably hydrogen or a $C_1$–$C_3$ alkyl group, and more preferably hydrogen, a methyl group or an ethyl group.

The group of the formula

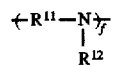

is included in formula (III) and has 1–5, preferably 1–4, more preferably 1–3 constituent units of the formula

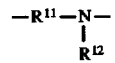

The group of formula (VIII) is derivable from the following polymers:

(7) Homopolymer consisting of one of the units of formula (IX).

(8) Random-, alternating- or block-copolymer consisting of two or more of different units of formula (IX).

The group $R^{13}$ in formula (III) is hydrogen or a $C_1$–$C_{30}$ hydrocarbon group. Preferred examples of $C_1$–$C_{30}$ hydrocarbon group include a $C_1$–$C_{24}$ straight or branched alkyl group, a $C_2$–$C_{24}$ straight or branched alkenyl group, a $C_5$–$C_{13}$ cycloalkyl or alkylcycloalkyl group, a $C_6$–$C_{18}$ aryl or alkylaryl group, or a $C_7$–$C_{19}$ arylalkyl group, and preferably hydrogen, $C_1$–$C_{12}$ straight or branched alkyl group and $C_6$–$C_{12}$ aryl or alkylaryl group, more preferably hydrogen, $C_1$–$C_6$ alkyl and phenyl group and $C_7$–$C_9$ alkylaryl group.

The group (C) of formula (III) is preferable in which $R^{11}$ is a $C_2$–$C_4$ alkylene group, $R^{12}$ is hydrogen or a $C_1$–$C_3$ alkyl group, $R^{13}$ is hydrogen, a $C_1$–$C_{12}$ straight or branched alkyl group, a $C_6$–$C_{12}$ aryl group or a $C_6$–$C_{12}$ alkylaryl group, and f is 1–4 and more preferable in which $R^{11}$ is an ethylene group, a propylene group (1-methylethylene and 2-methylethylene groups) and a trimethylene group. $R^{12}$ is hydrogen, a methylene group or a ethyl group. $R^{13}$ is hydrogen. $C_1$–$C_6$ alkyl or phenyl group, or $C_7$–$C_9$ alkylaryl group, and f is 1–3.

The group (D) of formula (IV) has been identified herein above, in which $R^{14}$ is a $C_2$–$C_4$ alkylene group including the above-mentioned "preferred alkylene groups of $R^6$" of which preferred are to be an ethylene group, a propylene group (1-methylethylene and 2-methylethylene), a trimethylene group, a butylene group (1-ethylethylene and 2-ethylethylene), a 1,2-dimethylethylene group, a 2,2-dimethyl ethylene group, a 1-methyltrimethylene group, a 2-methyltrimethylene group, a 3-methyltrimethylene group and a tetramethylene group, of which more particularly preferred are ethylene, propylene and trimethylene groups. $R^{15}$, $R^{16}$, $R^{17}$ and $R^{18}$ also already identified herein above are each hydrogen and a $C_1$–$C_{10}$ hydrocarbon group including a $C_1$–$C_{10}$ straight or branched alkyl group, a $C_2$–$C_{10}$ straight or branched alkenyl group, a $C_5$–$C_{10}$ cycloalkyl or alkylcycloalkyl group, a $C_6$–$C_{10}$ aryl or alkylaryl group and a $C_7$–$C_{10}$ arylalkyl group all of which have been already exemplified as preferred hydrocarbon of $R^2$, $R^3$, $R^4$ and $R^5$. Furthermore, $R^{15}$, $R^{16}$, $R^{17}$ and $R^{18}$ are each preferably hydrogen and a $C_1$–$C_6$, more preferably $C_1$–$C_3$ alkyl group. Y in formula (IV) as identified herein above is a methylene group, a methylene group substituted with a $C_1$–$C_{10}$ hydrocarbon, an imino group, an imino group substituted with a $C_1$–$C_{10}$ hydrocarbon or oxygen. Preferred examples of $C_1$–$C_{10}$ hydrocarbon include a $C_1$–$C_{10}$ straight or branched alkyl group, a $C_2$–$C_{10}$ straight or branched alkenyl group, a $C_5$–$C_{10}$ cycloalkyl or alkylcycloalkyl group, a $C_6$–$C_{10}$ aryl or alkylaryl group and a $C_7$–$C_{10}$ arylalkyl group, preferably a $C_1$–$C_6$, more preferably $C_1$–$C_3$ alkyl group. The group (D) of formula (IV) is preferable in which Y is methylene and $C_1$–$C_6$ alkyl-substituted methylene groups, imino and $C_1$–$C_6$ alkyl-substituted imino groups or oxygen more preferably imino and $C_1$–$C_3$ alkyl-substituted imino groups or oxygen.

If d in the formula (I) is equal to 1, g in the formula (IV) is 1. If d is equal to 2, g is 0 or 1. If d is equal to 2 and g is equal to 0, then N (nitrogen) in the formula (IV) corresponds to N in the formula (I) as indicated by the formula

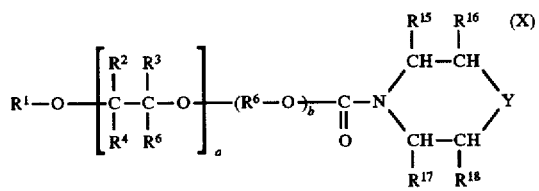

The group (D) of formula (IV) is preferable in which $R^{14}$ is a $C_2$–$C_4$ alkylene group, $R^{15}$, $R^{16}$, $R^{17}$ and $R^{18}$ are each hydrogen and a $C_1$–$C_6$ alkyl group, Y is a methylene group, a $C_1$–$C_6$ alkyl substituted methylene group, a imino group, a $C_1$–$C_6$ alkyl substituted imino group or oxygen and g is 1 if d is 1 and 0 or 1 if d is equal to 2 (if g is equal to 0, N in formula (IV) corresponds to N in formula (I)). The group (D) of formula (IV) is more preferable in which $R^{14}$ is an ethylene group, a propylene group (1-methylethylene and 2-methylethylene) or a trimethylene, $R^{15}$, $R^{16}$, $R^{17}$ and $R^{18}$ are each hydrogen or a $C_1$–$C_3$ alkyl group, Y is an imino group, a $C_1$–$C_3$ alkyl-substituted imino group or oxygen and g is 1 if d is 1 and 0 or 1 if d is equal to 2 (if g is equal to 0, N in formula (IV) corresponds to N in formula (I)).

The group X in formula (I) above identified may be chosen suitably from (A)–(D), in which instance if two of these groups are chosen, they may be the same or different. Such chosen groups X will be bonded directly to nitrogen (N) in formula (I) except where g is equal to 0 when group (D) is chosen, reference being made to formula (X). X in formula (I) is preferably (A), (C) or (D); more preferably either one of two chosen group X is (C) or (D) if d is equal to 1; either one of two chosen X group is (C) or (D) and the other is hydrogen if d is equal to 2; either one of two chosen group X is (D) in which g is equal to 1 and the other is hydrogen if d is equal to 2; and either one of two chosen group X is (D) in which g is equal to 0 and N in the formula (IV) corresponds to N in the formula (ID) if d is equal to 2.

A typical preferred embodiment of the inventive urethane compound having thus been described with respect to the various substituents in formula (I) may be represented in which $R^1$ is a $C_1$–$C_{12}$ straight or branched alkyl group or a $C_6$–$C_{12}$ aryl or alkylaryl group, one or two of $R^2$, $R^3$, $R^4$ and $R^5$ are the group of formula (II) and the remaining groups each are hydrogen or a $C_1$–$C_6$ alkyl group; $R^7$ and $R^8$ each are hydrogen, a $C_1$–$C_6$ alkyl group or a $C_2$–$C_6$ alkoxyalkyl group; $R^9$ is a $C_2$–$C_6$ alkylene group or a $C_2$–$C_8$ alkoxyalkyl-substituted ethylene group; $R^{10}$ is a $C_1$–$C_{24}$ alkyl group; e is an integer of between 0 and 30; $R^6$ is a $C_2$–$C_4$ alkylene group; a is an integer of between 1 and 100 and b is an integer of between 0 and 100, the sum of a and b being between 1 and 200; c is an integer of between 1 and 2 and d is an integer of between 1 and 2, the sum of c and d being 3; X is hydrogen (A), group (C) or group (D); $R^{11}$ is a $C_2$–$C_4$ alkylene group; $R^{12}$ is hydrogen or a $C_1$–$C_3$ alkyl group; $R^{13}$ is hydrogen, a $C_1$–$C_{12}$ straight or branched alkyl group or a $C_6$–$C_{12}$ aryl or alkylaryl; f is an integer of between 1 and 4; $R^{14}$ is a $C_2$–$C_4$ alkylene group; $R^{15}$, $R^{16}$, $R^{17}$ and $R^{18}$ each are hydrogen, or a $C_1$–$C_6$ alkyl group; Y is a methylene group, a $C_1$–$C_6$ alkyl-substituted methylene group, an imino group, a $C_1$–$C_6$ alkyl-substituted imino group or oxygen; and g is equal to 1if d is equal to 1, g is equal to 0 or 1 if d is equal to 2 (nitrogen N is shared in formulae (I) and (IV) if g is 0).

A more preferred embodiment of the inventive urethane compound is characterized in that $R^1$ is a $C_1$–$C_6$ alkyl or phenyl group or a $C_7$–$C_9$ alkylaryl group; either one of $R^2$, $R^3$, $R^4$ and $R^5$ is the group of formula (II) while the remaining three each are hydrogen or a $C_1$–$C_3$ alkyl group; $R^7$ and $R^8$ each are hydrogen or a $C_1$–$C_3$ alkyl group; $R^9$ is a $C_2$–$C_4$ alkylene group; $R^{10}$ is a $C_1$–$C_{12}$ alkyl group; e is an integer of between 0 and 20; $R^6$ is a $C_2$–$C_4$ alkylene group including an ethylene group, a propylene group (1-methylethylene and 2-methylethylene), a trimethylene group, a butylene group (1-ethylethylene and 2-ethylethylene), a 1,2-dimethylethylene group, a 2,2-dimethylethylene group, a 1-methyltrimethylene group, a 2-methyltrimethylene group, a 3-methyltrimethylene group and a tetramethylene group; a is an integer of between 5 and 50 and b is an integer of between 0 and 50, the sum of a and b being equal to between 5 and 100; c is an integer of 1 and d is an integer of 2; one of group X is hydrogen and the other is the group of formula (III) in which $R^{11}$ is an ethylene group, a propylene group (1-methylethylene and 2-methylethylene) or a trimethylene group; $R^{12}$ is hydrogen, a methyl or ethyl group; $R^{13}$ is hydrogen, a $C_1$–$C_6$ alkyl or phenyl group or $C_7$–$C_9$ alkylaryl group; f is an integer of between 1 and 3; or the group of formula (IV) in which $R^{14}$ is an ethylene group, a propylene group (1-methylethylene and 2-methylethylene) or a trimethylene; $R^{15}$, $R^{16}$, $R^{17}$ and $R^{18}$ each are hydrogen or a $C_1$–$C_3$ alkyl group; Y is an imino group, a $C_1$–$C_3$ alkyl-substituted imino group or oxygen; and g is equal to 1; or one of group X is the group of formula (IV) in which g is equal to 0 and N in formula (I) corresponds to N in formula (IV).

The urethane compound according to the invention may be prepared by any suitable methods known in the art. One such method is shown below.

Polymerization

An epoxy compound of the formula

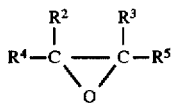 (XI)

where $R^2$, $R^3$, $R^4$ and $R^5$ are the same as indicated in formula (I)
is polymerized at about 80°–150° C. with addition of a reaction initiator of the formula

 (XII)

where $R^1$ is the same as in formula (I)
in the presence of a base such as potassium hydroxide and sodium hydroxide as a catalyst, whereby there may be obtained a polyoxyalkylene glycol derivative of the formula

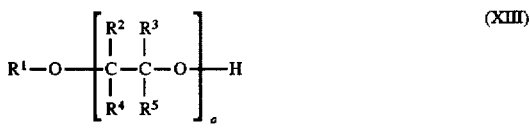 (XIII)

where $R^1$, $R^2$, $R^3$, $R^4$ and $R^5$ and a are the same as indicated in formula (I).

The oxygen-containing compound of formula (XII) may be used in the form of alcoxide or phenoxide with a base.

Alternatively, there may be used a mixture of the epoxy compound of formula (XI) and an oxylane compound of the formula $$R^6(=O)$$ (XIV)

where $R^6$ is the same as in formula (I).

The oxylan compound of the formula (XIV) is formed with two hydrogen atoms bonded to any two carbon atoms in the alkylene group $R^6$ substituted by one oxygen atom.

Further alternatively, the epoxy compound may be polymerized first with the above reaction initiator to obtain homopolymer thereof and then polymerized with the oxylane compound of formula (XIV), or this oxylane compound may be polymerized first with the above reaction initiator to obtain homopolymer thereof and then polymerized with the epoxy compound of formula (XI).

The above alternative polymerization procedures will result in the formation of a polyoxyalkylene glycol derivative of the formula

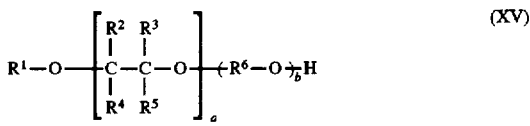 (XV)

where $R^1$, $R^2$, $R^3$, $R^4$ and $R^5$, a and b are the same as indicated in formula (I).

The polyoxyalkylene glycol derivative of the formula (XV) may be a block copolymer or a random copolymer.

Although not restricted, the ratio of the epoxy compound or the mixture thereof with the oxylane compound is preferably in the range of 5–100 mols per mol of the oxygen-containing compound.

Preferred examples of the epoxy compound of formula (XI) include methylglycidyl ether, ethylglycidyl ether, n-propylglycidyl ether, isopropylglycidy ether, n-butylglycidylcether, isobutylglycidyl ether, sec-butylglycidyl ether, tert-butylglycidyl ether, straight or branched pentylglycidyl ether, straight or branched hexylglycidyl ether, straight or branched heptylglycidyl ether, straight or branched octylglycidyl ether, straight or branched nonylglycidyl ether, straight or branched decylglycidyl ether, straight or branched undecylglycidyl ether, straight or branched dodecylglycidyl ether, straight or branched tridecylglycidyl ether, straight or branched tetradecylglycidyl ether, straight or branched pentadecylglycidyl ether, straight or branched hexadecylglycidyl ether, straight or branched heptadecylglycidyl ether, straight or branched octadecylglycidyl ether, vinylglycidyl ether, straight or branched propenylglycidyl ether, straight or branched butenylglycidyl ether, straight or branched pentenylglycidyl ether, straight or branched hexenylglycidyl ether, straight or branched heptenylglycidyl ether, straight or branched octenylglycidyl ether, straight or branched nonecylglycidyl ether, straight or branched decenylglycidyl ether, straight or branched undecenylglycidyl ether, straight or branched dodecenylglycidyl ether, straight or branched tridecenylglycidyl ether, straight or branched tetradecenylglycidyl ether, straight or branched pentadecenylglycidyl ether, straight or branched hexadecenylglycidyl ether, straight or branched heptadecenylglycidyl ether, straight or branched octadecenylglycidyl ether, phenylglycidyl ether, tolylglycidyl ether, xylylglycidyl ether, straight or branched propylphenylglycidyl ether, straight or branched butylphenylglycidyl ether, straight or branched pentylphenylglycidyl ether, straight or branched hexylphenylglycidyl ether, straight or branched heptylphenylglycidyl ether, straight or branched octylphenylglycidyl ether, straight or branched nonylphenylglycidyl ether, straight or branched decylphenylglycidyl ether, straight or branched undecylphenylglycidyl ether, straight or branched dodecylphenylglycidyl ether, straight or branched tridecylphenylglycidyl ether, 1,2-epoxy-3-methoxy-5-oxahexane, 1,2-epoxy-4,7-dioxaoctane, 4,5-epoxy-2,7-dioxaoctane, 1,2-epoxy-5-methyl-4,7-dioxaoctane, 1,2-epoxy-6-methyl-4,7-dioxaoctane, 1,2-epoxy-5-(2-oxapropyl)-4,7-dioxaoctane, 1,2-epoxy-3,5-bis(2-oxapropyl)-4,7-dioxaoctane, 1,2-epoxy-3,6-bis(2-oxapropyl)-4,7-dioxaoctane, 1,2-epoxy-6-methoxy-4,8-dioxaoctane, 1,2-epoxy-4,7,10-trioxaundecane, 1,2-epoxy-5-methyl-4,7,10-trioxaundecane, 1,2-epoxy-8-methyl-4,7,10-trioxaundecane, 4,5-epoxy-9-methyl-2,7,10-trioxaundecane, 1,2-epoxy-6,9-dimethyl-4,7,10-trioxaundecane, 1,2-epoxy-6,9-bis(2-oxapropyl)-4,7,10-trioxaundecane, 1,2-epoxy-4,7,10,13-tetraoxatetradecane, 4,5-epoxy-2,7,10-13-tetraoxateradecane, 7,8-epoxy-2,5,10-13-tetraoxateradecane, 7,8-epoxy-3,12-dimethyl-2,5,10,13-tetraoxateradecane and 1,2-epoxy-6,9,12-trimethyl-4,7,10-13-tetraoxatetradecane.

Preferred examples of the oxylane compound of formula (XIV) include ethylene oxide, propylene oxide, isobutylene oxide, 1-butene oxide (1,2-butylene oxide), 2-butene oxide, 1-pentene oxide, trimethylethylene oxide, 1-hexene oxide and tetramethylethylene oxide.

Chloroformation

The polyoxyalkylene glycol derivative of formula (XIII) or formula (XV) obtained as above may be subjected to chloroformation at room temperature in the presence of excess phosgene thereby obtaining chlorine-containing compounds of the formulae

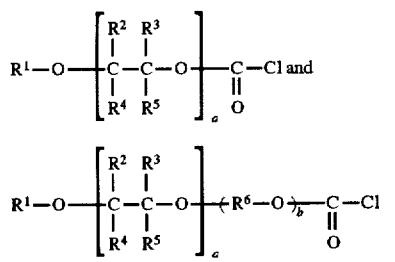

where $R^1$, $R^2$, $R^3$, $R_4$, $R^5$ and $R^6$ and a and b are the same as indicated in formula (I).

Carbamation

The compound of formula (XVI) or (XVI)' obtained as above may be subjected to carbamation reaction at below 5° C. with a nitrogen-containing compound of the formula

where X and d are the same as in formula (I).

The ratio of the chlorine-containing compound of formula (XVI) or (XVI)' to the nitrogen-containing compound (XVII) is optional, but the latter may be suitably greater in mol than the former.

The nitrogen-containing compound of formula (XVII) preferably includes ethylenediamine, propylenediamine (1,2-diaminopropane), trimethylenediamine (1,3-diaminopropane), dimethylaminopropylamine, diethylenetriamine, dipropylenetriamine, di(trimethylene)triamine, dimethylaminopropylenediamine, triethylenetetramine, tripropylenetetramine, tetraethylenepentamine, tetrapropylenepentamine, pentaethylenehexamine, pentapropylenehexamine, piperidine, 1-aminopiperidine, 4-aminomethylpiperidine, 1-(2-aminoethyl)piperidine, morpholine, 4-aminomorpholine, 4-(2-aminoethyl)morpholine, 4-(3-aminopropyl)morpholine, piperazine, 1-amino-4-methylpiperazine, 1-(2-aminoethyl)piperazine and 1-(3-aminopropyl)piperazine.

The inventive urethane compound may be added to fuel in an amount suitable to a particular application, usually in the range of 0.005–10, preferably 0.01–5 percent by weight based on total fuel composition. In the case of being added to internal combustion engine gasolines, the amount of the inventive urethane compound may be in the range of 0.005–5, preferably 0.01–4, more preferably 0.02–3 percent by weight based on total fuel composition in terms of enhanced detergent effect upon fuel intake systems and combustion chambers.

To provide enhanced detergent capabilities, there may be used one or more suitable other additives including an octane number improver such as alcohol such as methanol and ethanol, ether such as isopropylether, methyl tert-buthylether and methyl tert-amylether and aromatic amine; cetane number improvers such as nitric ester and organic peroxide; surface ignition inhibitors such as organic phosphate and organic phosphate halogenide; antioxidants including phenols such as 2,6-di-tert-butyl-p-cresol and aromatic amines such as phenyl-α-naphthylamine; metal deactivator such as a salicylidenic derivative; metal detergents such as metal sulfonate, metal phenate and metal salicylate; ashless detergent dispersants such as alkenyl succinimide, alkylpolyamine and polyetherpolyamine; antiicing agents such as glycol, glycerin and glycolether; microbiocides such as glycolether and boron compounds; combustion improvers such as metal naphthenate, metal sulfonate and alcohol sulfate; cold flow improvers such as ethylene-vinyl acetate copolymer and alkenyl succinamide; corrosion inhibitors such as aliphatic amine and alkenyl succinate; anti-static additives such as anion-based, cation-based or amphoteric surface active agent; and dyes such as an azo-dye. These additives may be added in an amount of less than 0.5, preferably less than 2 percent by weight based on total fuel composition.

The invention will be further described by way of the following examples.

SYNTHESIS 1

An autoclave (1 liter) was charged with 11.02 grams (0.05 mol) of nonylphenol and 2.81 grams (0.05 mol) of potassium hydroxide, followed by purging with nitrogen gas. The admixture was heated to 90° C. and then added with 81.37 grams (0.625 mol) of tert-butylglycidyl ether, 36.30 grams (0.625 mol) of propylene oxide and 100 milliliters of toluene. Reaction continued at 120° C. for 5 hours. The resulting reaction product was neutralized with chloric acid and extracted with toluene, followed by removal of toluene solvent, thereby providing 120 grams of polyoxyalkylene compound. 100 grams (0.04 mol measured by weight average molecular weight) of this compound mixed with 100 milliliters of toluene were added with 8.0 grams (0.081 mol) of liquid phosgene at 0° C. and reacted under dry ice reflex at room temperature for 12 hours. Excess phosgene was removed and solvent toluene was distilled out, whereupon there was obtained 102 grams chlorine-containing compound. 100 grams (0.05 mol) of this compound were added in droplets to a mixture of 100 milliliters toluene and 13.0 grams (0.1 mol) amino-ethyl morpholine cooled at 5° C. and reacted at this temperature for 3 hours. Upon completion of the reaction, unreacted aminoethyl morpholine, its chloride and solvent toluene were removed to provide 107 grams urethane compound. The resultant urethane compound was a dark orange oily liquid having a number average molecular weight of about 2,500. $^{13}$C-NMR analysis revealed the resultant compound to be a random copolymer having an average structure of the formula

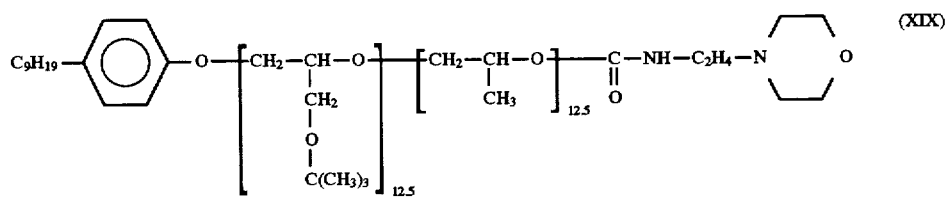

SYNTHESIS 2

The procedure of Synthesis 1 was followed except that 7.50 grams (0.05 mol) isobutylphenol was used in place of nonylphenol; 72.60 grams (0.625 mol) isopropylglycidyl ether was used in place of tert-butylglycidyl ether; 45.07 grams (0.625 mol) butylene oxide was used in place of propylene oxide; and 12.9 grams (0.1 mol) aminoethyl piperazine was used in place of aminoethyl morpholine. There was obtained 100 grams urethane compound which was a dark orange oily liquid having a number average molecular weight of about 2,500. $^{13}$C-NMR analysis the resultant compound to be a random copolymer having an average structure of the formula

SYNTHESIS 5

The procedure of Synthesis 1 was followed except that 1.60 grams (0.05 mol) methanol was used in place of nonylphenol; 72.11 grams (1.00 mol) tert-butylglycidyl ether was used; 8.5 grams (0.1 mol) piperazine was used in place of aminoethyl morpholine; and no propylene oxide was used. There was obtained 101 grams urethane compound in the form of a dark orange oily liquid having a number average molecular weight of about 2,600. $^{13}$C-NMR

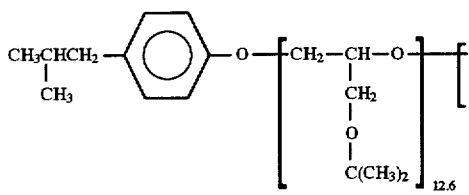

(XX)

SYNTHESIS 3

The procedure of Synthesis 1 was followed except that 3.71 grams (0.05 mol) tert-butanol was used in place of nonylphenol; 65.09 grams (0.50 mol) tert-butylglycidyl ether was used; 29.04 grams (0.50 mol) propylene oxide was used; and 6.0 grams (0.1 mol) ethylene diamine was used in place of aminoethyl morpholine. The resulting urethane compound was 93 grams dark orange oily liquid having a number average molecular weight of about 2,000. $^{13}$C-NMR analysis revealed the resultant compound to be a random copolymer having an average structure of the formula analysis revealed the resultant compound to be a polymer having an average structure of the formula

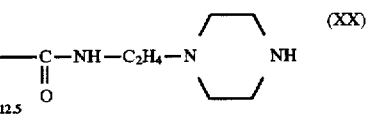

(XXIII)

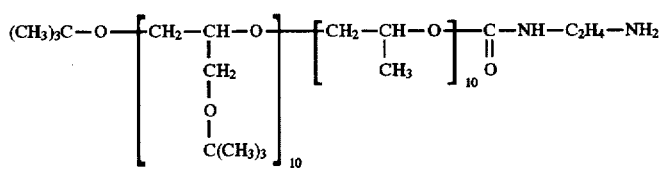

(XXI)

SYNTEHSIS 4

The procedure of Synthesis 1 was followed except that 5.41 grams (0.05 mol) methylphenol was used in place of nonylphenol; 46.57 grams (0.25 mol) 2-ethylhexyl glycidyl ether was used in place of tert-butylglycidyl ether; 58.08 grams (1.00 mol) propylene oxide was used; and 6.0 grams (0.1 mol) ethylene diamine was used in place of aminoethyl morpholine. The resulting urethane compound was 105 grams dark orange oily liquid having a number average molecular weight of about 2,100. $^{13}$C-NMR analysis revealed the resultant compound to be a random copolymer having an average structure of the formula

SYNTHESIS 6

The procedure of Synthesis 1 was followed except that 3.00 grams isopropanol was used in place of nonylphenol; 72.11 grams (1.00 mol) tert-butylglycidyl ether was used; 8.5 grams (0.1 mol) piperidine was used in place of aminoethyl morpholine; and no propylene oxide was used. There was obtained 101 grams urethane compound in the form of a dark orange oily liquid having a number average molecular weight of about 2,600. $^{13}$C-NMR analysis revealed the resultant compound to be a polymer having an average structure of the formula

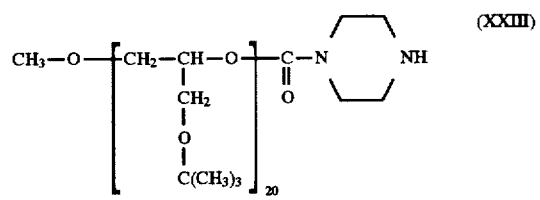

(XXII)

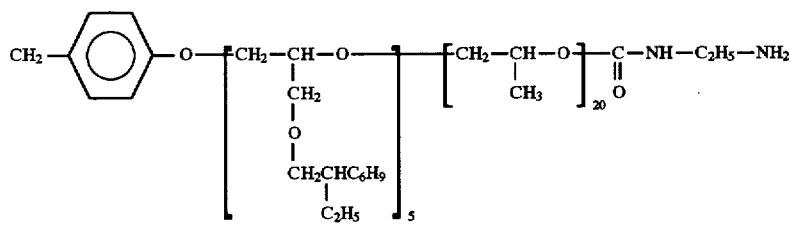

(XXII)

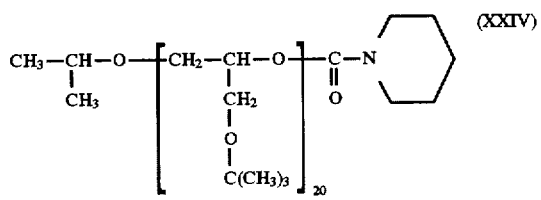

(XXIV)

INVENTIVE EXAMPLES 1–6 AND COMPARATIVE EXAMPLES 1–3

60 parts by volume of catalytically reformed gasoline, 30 parts by volume of catalytically cracked gasoline and 10 parts by volume of alkylate were mixed to produce a base gasoline of the following properties:

| | |
|---|---|
| Reid vapor pressure | 0.65 kgf/cm$^2$ |
| Specific gravity | 0.728 |
| Boiling range | 30°–190° C. |
| Octane number | 98.2 |

The base gasoline was added with each of the urethane compounds prepared as in Syntheses 1–6 above to provide fuel compositions (Inventive Examples 1–6) shown in Table 1.

Engine Evaluation Test

1. Cleanliness test of fuel intake system

The above base gasoline free of the inventive urethane compound was filled in a passenger car mounted with a new injector type engine of 2,000 ml total displacement. The car was run in the following mode, each cycle of which was repeated for a total of 200 hours.

Run Mode

Idling . . . 1 minute

Engine operating at 1,500 rpm with intake pressure of −200 mmHg . . . 30 minutes Engine operating at 2,700 rpm with intake pressure of −300 mmHg . . . 20 minutes Engine stopped . . . 9 minutes The engine was dismantled to measure the amount of deposits on intake valves. Then, the engine was re-assembled without removing the deposits and operated with each of fuels of the inventive examples according to the above mode repeatedly for 30 hours. The engine was again dismantled to determine deposits on intake valves. Cleanliness of intake systems was evaluated on the basis of differences in the amount of deposits between the first run with the starting gasoline alone and the second run with the inventive fuel compositions.

2. Evaluation test of combustion chamber deposit

A passenger car mounted with a new 2,000 ml total displacement jet engine was filled with each of the inventive fuel compositions and operated at an engine speed of 1,500 rpm with intake pressure of −150 mmHg and at cooling water temperature of 50° C. for a total travel time of 96 hours. The engine was thereafter disassembled to measure the amount of deposits in the combustion chamber in comparison with the amount of such deposits resulting from the use of the base gasoline alone.

Similar engine evaluation tests were made with Comparative Example 1 where the base gasoline alone was used and with Comparative Examples 2 and 3 where the base gasoline was added with polybutene amine detergents in place of the inventive urethane compound.

From the test results shown in Table 1 it will be seen that the use of commercially available polybutene amine detergents contributes to cleanliness of fuel intake system but conversely to increased deposits in the combustion chamber compared to the base gasoline alone. Whereas, the gasoline compositions incorporating the inventive urethane compounds exhibit significantly enhanced detergent effect upon fuel intake systems, while maintaining levels of combustion chamber deposits substantially comparable to those with the base gasoline alone.

TABLE 1

| | Inventive Examples | | | | | | Comparative Examples | | |
|---|---|---|---|---|---|---|---|---|---|
| | 1 | 2 | 3 | 4 | 5 | 6 | 1 | 2 | 3 |
| Composition (weight %) | | | | | | | | | |
| Starting base | [99.96] | [99.96] | [99.96] | [99.96] | [99.96] | [99.96] | [100.00] | [99.96] | [99.96] |
| Urethane compound | Synthesis 1 [0.04] | Synthesis 2 [0.04] | Synthesis 3 [0.04] | Synthesis 4 [0.04] | Synthesis 5 [0.04] | Synthesis 6 [0.04] | — | — | — |
| Other additives | — | — | — | — | — | — | — | polybutene amine [1] [0.04] | polybutene amine [2] [0.04] |
| Engine test | | | | | | | | | |
| varied deposits (mg) in intake systems | −50.3 | −48.2 | −60.6 | −58.8 | −50.1 | −40.8 | +20.4 | −27.2 | −49.5 |
| combustion chamber deposits [3] (mg) | +19.2 | +10.7 | −19.6 | +47.7 | +5.4 | +14.4 | — | +268.1 | +825.4 |

[1] Polybutene amine detergent 1
active component: imido (number average molecular weight about 3,000) of polybutenyl succinate and tetraethylene pentamine
[2] Polybutene amine detergent 2
active component: polybutenyl tetraethylene pentamine (number average molecular weight about 3,500)
[3] Differences compared with base gasoline alone

What is claimed is:

1. A fuel composition comprising a base gasoline blended with a urethane compound of the formula

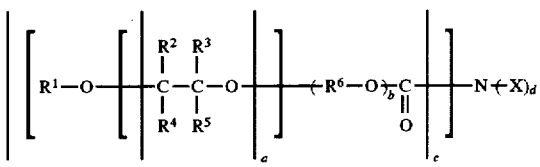

wherein $R^1$ is hydrogen or a $C_1$-$C_{30}$ hydrocarbon group, $R^2$, $R^3$, $R^4$ and $R^5$ each are selected from the group consisting of hydrogen, a $C_1$-$C_{10}$ hydrocarbon group, and a group of formula (II) below, provided that at least one of $R^2$, $R^3$, $R^4$ and $R^5$ is a group of formula (II), $R^6$ is a $C_2$-$C_6$ alkylene group, a is an integer of 1–100, b is an integer of 0–100, the sum of a and b being equal to 1–200, c is an integer of 1–3, d is an integer of 0–2, the sum of c and d being equal to 3, and X is selected from the group consisting of hydrogen, a $C_1$-$C_{30}$ hydrocarbon group, a group of formula (III) below and a group of formula (IV) below; said formula (II) being represented by

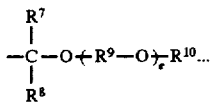

wherein $R^7$ and $R^8$ each are hydrogen, a $C_1$-$C_{10}$ hydrocarbon group or a $C_2$-$C_{10}$ alkoxyalkyl group, $R^9$ is a $C_2$-$C_6$ alkylene group or a $C_4$-$C_{10}$ alkylene group having an alkoxyalkyl substituent, $R^{10}$ is hydrogen or a $C_1$-$C_{30}$ hydrocarbon group, and e is an integer of 0–50;
said formula (III) being represented by

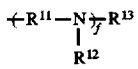

wherein $R^{11}$ is a $C_2$-$C_6$ alkylene group, $R^{12}$ is hydrogen or a $C_1$-$C_4$ alkyl group, $R^{13}$ is hydrogen or a $C_1$-$C_{30}$ hydrocarbon group, and f is an integer of 1–5;
and said formula (IV) being represented by

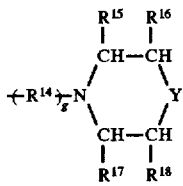

wherein $R^{14}$ is a $C_2$-$C_6$ alkylene group, $R^{15}$, $R^{16}$, $R^{17}$ and $R^{18}$ each are hydrogen or a $C_1$-$C_{10}$ hydrocarbon group, Y is a methylene group, a $C_1$-$C_{10}$ hydrocarbon-substituted methylene group, an imino group, a $C_1$-$C_{10}$ hydrocarbon-substituted imino group or oxygen, g is 1 if d is equal to 1 and 0 or 1 if d is equal to 2, and if g is equal to 0, N in formula (IV) also corresponds to N in formula (I).

2. A fuel composition according to claim 1 wherein said urethane compound is represented by the formula

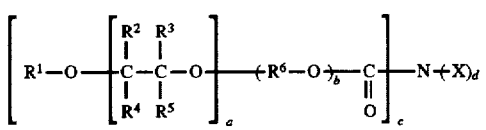

wherein $R^1$ is a $C_1$-$C_{12}$ straight or branched alkyl group or a $C_6$-$C_{12}$ aryl or alkylaryl group; $R^2$, $R^3$, $R^4$ and $R^5$ each are selected from the group consisting of hydrogen, a $C_1$-$C_6$ alkyl group and a group of formula (II) below, with the proviso that one or two of $R^2$, $R^3$, $R^4$ and $R^5$ are groups of formula (II); $R^6$ is a $C_2$-$C_4$ alkylene group; a is an integer of between 1 and 100, b is an integer of between 0 and 100, the sum of a and b being 1 and 200, c is an integer of between 1 and 2, d is an integer of between 1 and 2, the sum of c and d being 3; and X is hydrogen, a group of formula (III) below or a group of formula (IV) below;
said formula (II) being represented by

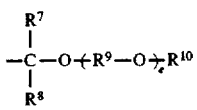

wherein $R^7$ and $R^8$ each are hydrogen, a $C_1$-$C_6$ alkyl group or a $C_2$-$C_6$ alkoxyalkyl group; $R^9$ is a $C_2$-$C_6$ alkylene group or a $C_2$-$C_8$ alkoxyalkyl-substituted ethylene group; $R^{10}$ is a $C_1$-$C_{24}$ alkyl group; e is an integer of between 0 and 30;
said formula (III) being represented by

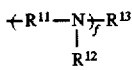

wherein $R^{11}$ is a $C_2$-$C_4$ alkylene group, $R^{12}$ is hydrogen or a $C_1$-$C_3$ alkyl group, $R^{13}$ is hydrogen or a $C_1$-$C_{12}$ straight or branched alkyl group or a $C_6$-$C_{12}$ aryl or alkylaryl group; f is an integer of between 1 and 4;
and said formula (IV) being represented by

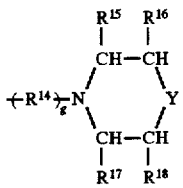

where $R^{14}$ is a $C_2$-$C_4$ alkylene group; $R^{15}$, $R^{16}$, $R^{17}$ and $R^{18}$ each are hydrogen or a $C_1$-$C_6$ alkyl group; Y is a methylene group, a $C_1$-$C_6$ alkyl-substituted methylene group, an imino group, a $C_1$-$C_6$ alkyl-substituted imino group or oxygen; and g is equal to 1 if d is equal to 1, g is equal to 0 or 1 if d is equal to 2 (nitrogen N is shared in formulae (I) and (IV) if g is 0).

3. A fuel composition according to claim 1 wherein said urethane compound is represented by the formula

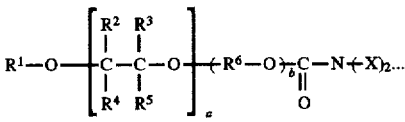

wherein $R^1$ is a $C_1$-$C_6$ alkyl or phenyl group or a $C_7$-$C_9$ alkylaryl group; one of $R^2$, $R^3$, $R^4$ and $R^5$ is the group of formula (II) below while the remaining three each are hydrogen or a $C_1$-$C_3$ alkyl group; $R^6$ is a $C_2$-$C_4$ alkylene group selected from the group consisting of ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene and tetramethylene; a is an integer of between 5 and 50 and b is an integer of between 0 and 50, the sum of a and b being equal to between 5 and 100; one of group X is hydrogen and the other is the group of formula (III) below or formula (IV) below;
said formula (II) being represented by

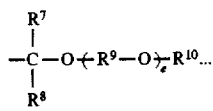 (II)

wherein $R^7$ and $R^8$ each are hydrogen or a $C_1$–$C_3$ alkyl group; $R^9$ is a $C_2$–$C_4$ alkylene group; $R^{10}$ is a $C_1$–$C_{12}$ alkyl group; e is an integer of between 0–20;
said formula (III) being represented by

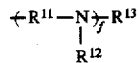 (III)

wherein $R^{11}$ is selected from the group consisting of ethylene, 1-methylethylene, 2-methylethylene and trimethylene; $R^{12}$ is hydrogen, a methyl or ethyl group; $R^{13}$ is hydrogen, a $C_1$–$C_6$ alkyl or phenyl group or $C_7$–$C_9$ alkylaryl group; f is an integer of between 1 and 3;
and said formula (IV) being represented by

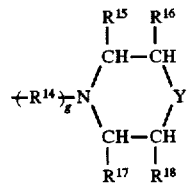 (IV)

wherein $R^{14}$ is selected from the group consisting of ethylene, 1-methylethylene, 2-methylethylene and trimethylene; $R^{15}$, $R^{16}$, $R^{17}$ and $R^{18}$ each are hydrogen or a $C_1$–$C_3$ alkyl group; Y is an imino group, a $C_1$–$C_3$ alkyl-substituted imino group or oxygen and g is 1.

4. A fuel composition according to claim 1 wherein said urethane compound is represented by the formula

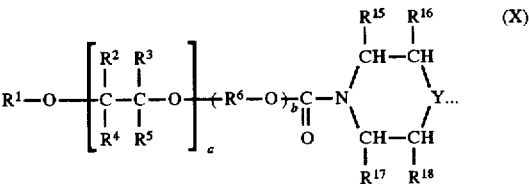 (X)

wherein $R^1$ is a $C_1$–$C_6$ alkyl or phenyl group or a $C_7$–$C_9$ alkylaryl group; one of $R^2$, $R^3$, $R^4$ and $R^5$ is the group of formula (II) below while the remaining three each are hydrogen or a $C_1$–$C_3$ alkyl group; $R^6$ is a $C_2$–$C_4$ alkylene group selected from the group consisting of ethylene, 1-methylethylene, 2-methylethylene, trimethylene, 1-ethylethylene, 2-ethylethylene, 1,2-dimethylethylene, 2,2-dimethylethylene, 1-methyltrimethylene, 2-methyltrimethylene, 3-methyltrimethylene and tetramethylene; $R^{15}$, $R^{16}$, $R^{17}$ and $R^{18}$ each are hydrogen or a $C_1$–$C_3$ alkyl group; Y is an imino group, a $C_1$–$C_3$ alkyl-substituted imino group or oxygen; a is an integer of between 5 and 50 and b is an integer of between 0 and 50, the sum of a and b being equal to between 5 and 100; said formula II being represented by

 (II)

wherein $R^7$ and $R^8$ each are hydrogen or a $C_1$–$C_3$ alkyl group; $R^9$ is a $C_2$–$C_4$ alkylene group; $R^{10}$ is a $C_1$–$C_{12}$ alkyl group; and e is an integer of between 0 and 20.

* * * * *

UNITED STATES PATENT AND TRADEMARK OFFICE
CERTIFICATE OF CORRECTION

PATENT NO. : 5,755,833
DATED : May 26, 1998
INVENTOR(S) : Noboru Ishida et al.

It is certified that error appears in the above-indentified patent and that said Letters Patent is hereby corrected as shown below:

Column 21, lines 4 to 10, formula (I) should appear as follows:

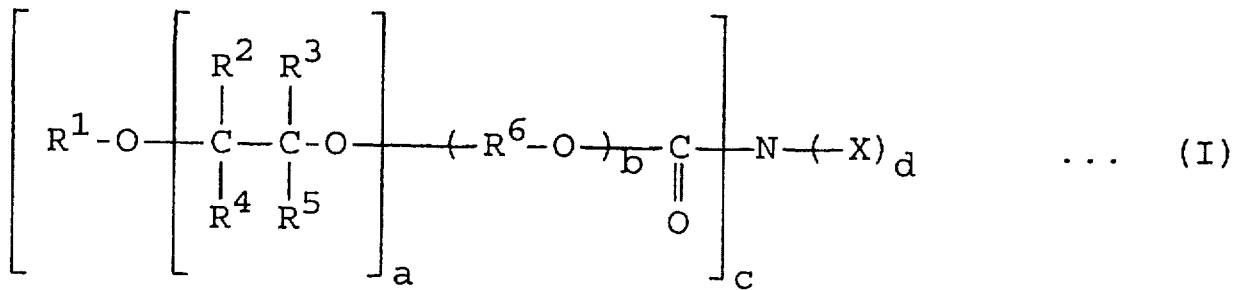

Signed and Sealed this

Twenty-fifth Day of August, 1998

Attest:

BRUCE LEHMAN

*Attesting Officer*   *Commissioner of Patents and Trademarks*